United States Patent [19]

Horlington et al.

[11] 4,425,345

[45] Jan. 10, 1984

[54] PHARMACEUTICAL COMPOSITION CONTAINING TRIAMTERENE

[75] Inventors: Michael Horlington, Bishops Stortford; Lindsey V. Scott, London, both of England

[73] Assignee: Smith and Nephew Associated Companies Limited, England

[21] Appl. No.: 328,729

[22] Filed: Dec. 8, 1981

Related U.S. Application Data

[63] Continuation-in-part of Ser. No. 287,356, Jul. 27, 1981.

[30] Foreign Application Priority Data

| Aug. 1, 1980 [GB] | United Kingdom | 8025286 |
| Jan. 8, 1981 [GB] | United Kingdom | 8100521 |
| Apr. 2, 1981 [GB] | United Kingdom | 8110448 |
| Jul. 21, 1981 [GB] | United Kingdom | 8122410 |
| Jul. 28, 1981 [GB] | United Kingdom | 8123222 |

[51] Int. Cl.$^3$ .......................................... A61K 31/505
[52] U.S. Cl. .................................................... 424/251
[58] Field of Search .......................................... 424/251

[56] References Cited

U.S. PATENT DOCUMENTS

| 3,081,230 | 3/1963 | Weinstock et al. | 424/251 |
| 3,870,791 | 3/1975 | Haddad et al. | 424/361 |
| 4,187,307 | 2/1980 | Paris et al. | 424/251 |
| 4,285,947 | 8/1981 | Higuchi et al. | 424/251 |

FOREIGN PATENT DOCUMENTS 932256  7/1963  United Kingdom .

OTHER PUBLICATIONS

Martindale, The Extra Pharmacopoeia, 27th Ed., (1977), pp. 569–570.

*Primary Examiner*—Douglas W. Robinson
*Attorney, Agent, or Firm*—Jacobs & Jacobs

[57] ABSTRACT

A sterile, non-irritant, non-toxic aqueous solution adapted for topical administration to the eye which contains 2,4,7-triamino-6-phenylpteridine rendered soluble by a solubilizing amount of a xanthine derivative. The composition may be used to treat ocular hypertension and glaucoma.

30 Claims, No Drawings

PHARMACEUTICAL COMPOSITION CONTAINING TRIAMTERENE

This is a continuation-in-part of Application U.S. Ser. No. 287,356 filed July 27, 1981 and entitled "Pharmaceutical Composition"

This invention relates to pharmaceutical compositions suitable for topical application to the eye which contain triamterene Glaucoma is a degenerative disease of the eye manifest inter alia by an elevated intra-ocular pressure in the eye. Ocular hypertension, that is the condition of elevated intra-ocular pressure, is believed by many authorities to represent an early phase in the onset of glaucoma. One method of treatment of ocular hypertension and glaucoma is to administer to the subject a pharmacologically active compound capable of reducing the intra-ocular pressure. A number of compounds presently employed to treat ocular hypertension and glaucoma are not entirely satisfactory due at least in part to side effects such as pupil contraction and the like. Clearly it would be desirable to provide an agent which could be applied topically to treat ocular hypertension and glaucoma without an unacceptable level of such side effects. It has now been found that the topical administration of triamterene to the eye can reduce the intra-ocular pressure therein without producing an unacceptable level of side effects such as pupil constriction.

The preparation of triamterene (2,4,7-triamino-6-phenylpteridine) is described by Spickett and Timmins in J. Chem. Soc. 1954 2887-95 and compositions suitable for oral use of triamterene as a diuretic are described in U.S. Pat. No. 3,081,230. Some sixteen years ago a report occurred that an oral dose of 60-240 mg. of triamterene lead in some subjects to a decrease in intra-ocular pressure which was moderate and of slow onset. However use of a systemic dose of this magnitude leads to triamterene exhibiting a pronounced undesired systemic diuretic and natriuretic effect which might lead to an electrolyte imbalance within the patient. (Sakanoue, M. et. al. Jap. J. Clinical Ophthalmolgy 1964, 18 1029-34). In a subsequent report patients received 100 mg of triamterence orally and the results showed no consistent ocular pressure-lowering effect and some subjects actually exhibited an increase in ocular pressure. (Peczon, Grant Amer. J. Ophthalmol. 1968, 64 680-3). Some eighteen years ago a report occurred that triamterene given orally in amounts of 50 and 100 mg together with known orally-active antiglaucoma agents such as acetazolamide and hydrochlorthiazide decreased the intra-ocular pressure in the glaucomatous eye. No suggestion was made that triamterene alone had any effect on intra-ocular pressure. The use of such a systemic dose causes triamterene to exhibit its unwanted diuretic properties. (Nicosia, A and Petrosillo, O., Atti XLVII Cong. Soc. Oftal. Ital, 1963, publ. 1964 21, 283-292). Thus until now there has been no reason to suppose that triamterene could be used to effectively lower intra-ocular pressure without systemic side effects. However it has now been found that the topical administration of triamterene to the eye results in a rapid and significant lowering of intra-ocular pressure and that this occurs without systemic side effects such as diuresis and without local side effects such as pupil constriction.

Accordingly the present invention provides a pharmaceutical composition adapted for administration to the eye which composition contains triamterene together with a carrier therefor.

In order to be suitable for application to the eye the topical composition should be sterile, non-irritant and non-toxic to the eye.

From the foregoing the skilled worker will appreciate that this invention provides a sterile, non-irritant, non-toxic composition adapted for topical administration to the eye for the treatment of glaucoma which composition comprises triamterene together with a carrier therefor.

Suitable forms of the composition include aqueous solutions, aqueous suspensions, oily solutions, oily suspensions, ointments, emulsions and sustained release implants. In general it is preferred to use aqueous solutions or aqueous suspensions for the compositions of this invention. Such aqueous forms preferably also contain an agent which increases the amount of triamterene in suspension (a suspending agent) or solution (a solubilising agent) as described hereinafter.

Most desirably the composition of this invention will be an aqueous solution.

Aqueous forms of this composition are normally rendered isotonic; that is they will desirably have a tonicity equivalent to an aqueous solution containing 0.7 to 1.2% of sodium chloride, more suitably equivalent to 0.8 to 1.1% of sodium chloride and most suitably equivalent to an aqueous solution containing 0.9% of sodium chloride.

Sterile compositions may be conveniently prepared by (a) sterilising the finely divided triamterene by dry heat over a period of time at elevated temperature for example by heating to 160° C. for 1 hour, allowing the powder to cool and storing aseptically, (b) sterilising the liquid components of the composition by either filtration through a 0.22 micron cellulose ester membrane or by subjecting the solution to heat and pressure such as autoclaving at 116° C. for 30 minutes under 10 psi pressure. The two sterile components are combined in the desired proportions under aseptic conditions and filled into sterile containers.

Surprisingly it has been found that triamterene may be of use over an unusually wide range of concentrations, for example 0.001 to 5% but more usually from 0.01 to 1%.

The amount of triamterene present in the compositions of this invention will vary depending on the ability of the triamterene to be taken into the eye. Thus for aqueous solutions of the invention a lower amount of triamterene will be present, suitably from 0.001 to 0.25%, aptly from 0.005 to 0.2% and more suitably from 0.01 to 0.1% (% terms when used herein are expressed on a wt/wt basis unless shown otherwise). The amount of triamterene present in a suspension will tend to be larger than that of the solution to acheive the same fall in intra-ocular pressure. Suitably aqueous suspensions of the invention will contain from 0.01 to 1%, more suitably 0.02 to 0.75% and preferably from 0.05 to 0.5%.

It is normally preferred in the treatment of glaucoma to employ an aqueous solution. Triamterene is a highly insoluble material. It has in the past proved impracticable to provide a solution of triamterene containing more than about 0.15% and that required the employment of considerable quantities of acid (see West German Offenlegenschrift No. 2918319). Such solutions may be employed in the eye but can cause irritation. Clearly it is desirable to provide aqueous solutions that do not necessitate the use of highly acidic solutions and are generally at a pH of not less than 4.5, more aptly at a pH not less than 6 and preferably at a pH of approximate neutrality, i.e. pH 7. The pH of such solutions should also not in general be greater than 8.5 and preferably not greater than pH 8. It has been found that such solutions may be prepared by using solubilising agents. It is particularly surprising that such solutions may contain more than 0.1% of triamterene without having to resort to highly acidic solutions.

Favourably the aqueous solutions of this invention will contain a solubilising agent such as polyvinyl pyrrolidone, polyalkylene glycol, non-ionic surfactants or a polyacrylic acid which has been lightly crosslinked with triallyl sucrose in combination with a non-ionic surfactant. An apt solubilising agent is a polyvinyl pyrrolidone. Suitable polyvinyl pyrrolidones are those with a number average molecular weight below 40,000, more suitable are those with a number average molecular weight below 5000 and a particularly preferred polyvinyl pyrrolidone is one having a number average molecular weight of 2,500. Such a polyvinyl pyrrolidone is exemplified by Kollidon 12PF (Registered Trade Mark of BASF). Suitably the amount of polyvinyl pyrrolidone present is from 0.5 to 55%, preferably is from 15 to 52% and most preferably is from 20 to 50%.

Another apt solubilising agent is a polyalkylene glycol. The preferred polyalkylene glycol is polyethylene glycol, such as the Carbowaxes (Carbowax is a registered trade mark of Union Carbide). These polyethylene glycols have a molecular weight ranging from about 200 to about 6000. Particularly preferred for aqeuous solutions of the present invention are those of a high molecular weight of 4000 to 6000 such as those known as Carbowax 4000 or Carbowax 6000. The amount of polyalkylene glycol present is suitably from 1 to 40%, more suitably is from 10 to 30% and is preferably from 15 to 25%.

Suitable non-ionic surfactants for use as solubilising agents for triamterene either alone or with a polyacrylic acid include polyoxyethylated sorbitan fatty acid ester (commonly called polysorbates, more commonly called Tweens) and polyoxyethylene-polyoxypropylene diol block copolymers (commonly known as Poloxamers, more commonly known as Pluronics). A preferred polyoxyethylated sorbitan fatty acid ester is polyoxyethylene sorbitan mono-oleate (known as Tween 80). Preferred polyoxyethylene-polyoxypropylene diol block copolymers are known as Pluronic L62, Pluronic F108 and Pluronic F68. Pluronic L62 is a diol block copolymer in which the polymer contains 20% polyoxyethylene units in the total molecule and a molecular weight of approximately 2190, whilst Pluronic F108 is a diol block copolymer in which the polymer contains 80% polyoxyethylene units in the total molecule and a molecular weight of approximately 8750. Suitably the non-ionic surfactant is present in an amount from 1 to 30%, more suitably the amount is from 5 to 25% and preferably is 10 to 20%.

A further suitable solubilising system for triamterene is a combination of a non-ionic surface active agent as defined above together with a poly acrylic acid lightly cross-linked with triallyl sucrose. Such polyacrylic acids include those known as the Carbopols (Registered Trade Mark of B. F. Goodrich). A preferred Carbopol is Carbopol 941. To be effective as a solubilising agent the Carbopols must be neutralised by a suitable aqueous solution of a base. Such aqueous solutions include those of the alkali metal hydroxides, ammonia and other nitrogenous bases such as ethanolamine and the like. Suitably the amount of polyacrylic acid lightly cross-linked with triallyl sucrose present is 0.01 to 5%, more suitably is from 0.05 to 0.5% and is preferably 0.08 to 0.12%. Suitably the amount of non-ionic surfactant also present is 1 to 30%, more suitably 5 to 25% and preferably is 10 to 20%.

Further suitable solubilising systems for triamterene include combinations of polyalkylene glycol, polyvinyl pyrrolidone and non-ionic surface active agent either as a combination of three together or as a combination of any two types of agent. Preferred polyalkylene glycols are polyethylene glycols having a molecular weight range of 200 to 6000, particularly a polyethylene glycol of MW 6000. Preferred polyvinyl pyrrolidones are those with a number average molecular weight below 40,000, particularly preferred is a polyvinyl pyrrolidone with a number average molecular weight below 5000. Preferred non-ionic surface active agents are polyoxyethylene-polyoxypropylene diol block copolymers (commonly known as Pluronics). Suitably when in combination with polyvinyl pyrrolidone and/or a non-ionic surface active agent the polyalkylene glycol is present in an amount from 1 to 40%, more suitably from 10 to 30% and preferably 15 to 25%; suitably when in combination with polyalkylene glycol and/or non-ionic surface active agent the amount of polyvinyl pyrrolidone present is from 0.5 to 55%, is more suitably 15 to 52% and most preferably is from 20 to 50%; suitably when in combination with polyalkylene glycol and/or polyvinyl pyrrolidone the non-ionic surface active agent is present in an amount from 1 to 30%, more suitably from 5 to 25% and most preferably is 10 to 20%.

Surprisingly it has now been found that triamterene may be solubilised by employing a class of agents that neither unduly increase the viscosity of the solution nor unduly increase the surfactant properties of the solution. This class of agents which may be thus employed are water soluble xanthine derivatives.

Thus in a favoured aspect this invention provides a sterile, non-irritant, non-toxic aqueous solution adapted for topical administration to the eye for the treatment of glaucoma which composition comprises triamterene and a solubilising xanthine.

The solubilising xanthine is normally a dimethylxanthine which optionally may be substituted by a hydrophilic group or (less preferably) a methyl group. Most aptly the xanthine is a 1,3-dimethylxanthine unsubstituted or substituted at the 7 position by a methyl group or more aptly substituted at the 7-position by a hydrophilic group such as a 2-hydroxypropyl group (thereby proxyphylline), a 2,3-dihydroxypropyl group, (thereby dyphylline, a 2-hydroxyethyl group (thereby hydroxyethyl theophylline, also commonly known as etophylline), a carboxymethyl group (thereby theophyllinylacetic acid), a N,N-diethylaminoethyl group (thereby etamiphylline) or the like. Less favourably the xanthine is a 3,7-dimethylxanthine unsubstituted or substituted at the 1-position for example pentoxyphylline.

Particularly apt solubilising xanthines are caffeine, proxyphylline, dyphylline and hydroxyethyl theophylline. These agents may be present in any convenient solubilsing amount, for example from 0.1% to 10% (or up to the solubility limit), more usually from 1% to 8%.

Preferably the solution will contain from 2% to 7.5% of proxyphylline or dyphylline.

The xanthine solubilising agent may be present as the sole solubilising agent or less aptly other solubilising agents such as those hereinbefore described may also be included.

The use of solubilising agents allows for the preparation of solutions containing more than 0.2% and even more than 0.25% of triamterene, for example 0.3%. It is particularly surprising that such solutions can be formed without resorting to highly acid pH.

It will be appreciated from the foregoing that the range of concentrations of triamterene for which the presence of a solubilising amount of xanthine is particularly apt is from 0.05 to 0.4% of triamterene. Preferably the concentration of triamterene in aqueous solution solubilized by the xanthine will be between 0.1 and 0.3%.

The pH of the xanthine containing solutions may be varied as described hereinbefore with respect to solutions as a class but in general the lower the pH the more triamterene that can be taken into solution. However as hereinbefore described it is preferred not to use a highly acidic solution i.e. a solution of pH less than 4.5 and more aptly not less than 5 and not greater than 8.5 and preferably not greater than pH 8. Indeed if a buffer is employed it is preferred that the pH will be from 5.0 to 8.0 and preferably 6.0 to 7.5, for example 7.

In certain circumstances it may be preferred to use a salt of triamterene to provide the triamterene. Such salts include those with hydrochloric, phosphoric, acetic and gluconic acids. Other suitable salts include those with lactic, glutamic, glycerophosphoric, aspartic or the like acid. In general these salts are prepared in situ and do not exist as true salts outside the formulation; i.e. the solutions of triamterene may be rendered slightly acidic using such acids so that a salt is notionally formed.

Normally and preferably aqueous solutions and suspensions of the invention will contain tonicity adjusting agents, for example sodium chloride, potassium chloride, glycerol, propylene glycol, urea or dextrose to render the solution or suspension isotonic or substantially isotonic with tear fluid, that is to say, to give the compositions a tonicity equivalent to an aqueous solution containing from 0.8 to 1.1 of a sodium chloride and most suitably equivalent to an aqueous solution containing 0.9% of sodium chloride.

Normally and preferably aqueous solutions of the invention will contain an ophthalmologically acceptable preservative (sometimes referred to as a bactericidal agent) to maintain the sterility of the solution during daily use. It is known in the art that certain preservatives are affected by the presence of surface active agents, viscosity increasing agents and the like and naturally such agents will be selected to be mutually compatible in the conventional manner. Preferred preservatives for use in the presence of for example polyvinyl pyrrolidone include the phenylmercuric salts such as phenylmercuric nitrate or phenylmercuric acetate; the amount of such bactericidal agents is from 0.001 to 0.004%, and most preferably is 0.002%. Preferred bactericidal agents for use in the presence of for example polyethylene glycol include phenyl ethanol in an amount 0.25 to 0.75% and most preferably 0.4 to 0.6%.

Particularly apt ophthalmically acceptable preservatives for use in aqueous solutions of the invention are antibacterially effective quaternary ammonium compounds. Such quaternary ammonium compounds include benzalkonium salts such as its chloride, benzethonium chloride, cetyl pyrridinium chloride and the like. The preferred quaternary ammonium compound is benzalkonium chloride. Suitably the amount of quaternary ammonium compound present is from 0.005 to 0.04%, more suitably is from 0.0075 to 0.025% and is preferably from 0.01 to 0.02% of the composition.

Optionally the aqueous solutions of the present invention will contain a buffering agent to maintain the pH of the solution from 5.0 to 8.0 and preferably from 6.0 to 7.5. Suitable buffering agents include those based on mixtures of potassium dihydrogen phosphate and disodium hydrogen phosphate and other systems known to provide solutions having such pH values.

In aqueous suspensions of triamterene, the triamterene will be dispersed evenly throughout. The triamterene will be in finely divided form. In this state of subdivision of the triamterene 99% of the particles are less than 30 microns in diameter and 90% are less than 10 microns in diameter. Most aptly the particles will have diameters in the range 1 to 5 microns.

Generally the composition of this invention will contain a suspending agent for the finely divided triamterene. Suitable suspending agents include cellulosic or polysaccharide derivatives (such as hydroxyethylcellulose, hydroxypropyl cellulose, carboxymethylcellulose or a xanthan gum) or a water-soluble polymer (such as polyvinyl alcohol or polyvinyl pyrrolidone or a polyacrylic acid lightly cross-linked with triallyl sucrose). A most favoured suspending agent is one of the polyacrylic acids lightly cross-linked with triallyl sucrose known as Carbopols (registered trade mark of B. F. Goodrich). A preferred Carbopol is Carbopol 941. To be effective as a suspending agent the Carbopols must be neutralised by a suitable base. Suitable bases include aqueous solutions of alkali metal hydroxides, ammonia or other nitrogenous organic bases. A preferred base is an aqueous solution of an alkali metal hydroxide. A most preferred base is sodium hydroxide solution. The Carbopols are neutralised during the preparation of the suspension to give the suspension a pH value of between 6.5 and 8. Suitably the suspending agent will be present in an amount between 0.01 to 5% depending on the kind of agent used. Preferably the amount of suspending agent present is 0.05 to 2%.

Generally the aqueous suspension of the present invention will contain a surface active agent to encourage wetting of the surface of the particles of the finely divided triamterene by water, thus aiding the even dispersion of the triamterene throughout the suspension. Favoured surface active agents are polyoxyethylated sorbitan fatty acid esters (commonly called Tweens) or polyoxypropylene-polyoxyethylene diol block copolymers (commonly called Pluronics). Particularly preferred are polyoxyethylene sorbitan mono-oleate (commonly called Tween 80) and a polyoxypropylene-polyoxyethylene diol block copolymer of molecular weight 4375, having 40% of ethylene oxide units in the polymer (commonly called Pluronic L64).

Suitably the amount of surface active agent present is from 0.01 to 0.5% and preferably from 0.02 to 0.2%.

Normally the aqueous suspensions of the present invention will contain tonicity adjusting agents, for example sodium chloride, potassium chloride, glycerol or propylene glycol to render the suspension isotonic or approximately isotonic with tear fluid, that is to say to give the composition a tonicity equivalent to an aqueous solution containing from 0.8 to 1.1% sodium chloride and most suitably 0.9% sodium chloride. The use of sodium chloride or other ionic tonicity agents may render some suspensions unstable. In these cases it is preferred that a non-ionic tonicity adjusting agent such as glycerol or propylene glycol is used.

Generally the aqueous suspensions of the present invention will also contain an ophthalmically acceptable preservative or bactericidal agent to maintain sterility of the suspension during daily use over a period of up to thirty days. As mentioned hereinbefore it is known that bactericidal agents and suspending agents are in some cases incompatible, for example an insoluble salt may be formed between the large anion of a suspending agent and a large cation of a bactericidal agent such as the benzalkonium ion. Thus it is preferred that if a Carbopol is used as a suspending agent a non-cation generating bactericidal agent or preservative system is used. Suitable bactericidal agents include phenyl ethanol, phenoxy ethanol, chlorobutanol or thiomersal. A preferred preservative system is a combination of phenylethanol in an amount from 0.25 to 0.75 and thiomersal in an amount from 0.005 to 0.02. A preferred combination is 0.5% phenylethanol and 0.01% thiomersal.

Normally the aqueous suspension of the invention will contain a buffering agent to maintain the pH of the suspension from 5.0 to 8.0 and preferably from 6.0 to 7.5. Suitable buffering agents include those described hereinbefore.

Isotonicity adjusting agents will be employed in aqueous suspensions as described hereinbefore with respect to aqueous solutions.

Oily suspensions of triamterene include suspensions in solvents such as castor oil and such compositions will suitably contain from 0.01 to 5% of finely divided triamterene, more favourably 0.02 to 0.75% and most preferably 0.05 to 0.5% of triamterene.

Ointments in accordance with the invention will comprise ointment bases suitable for topical application to the eye and contain suitably from 0.01 to 5% of finely divided triamterene.

Ocular implants may comprise triamterene in a finely divided form in a suitable soluble or insoluble material. Soluble forms for example where the finely divided triamterene is suspended in a polyvinyl alcohol film, dissolve and so do not need to be removed later, whereas the insoluble forms are removed from the eye after the medicament has diffused from the form. Suitably the ocular implant will contain from 0.01 to 5% of finely divided triamterene.

The present invention also provides a method for reducing the intra-ocular pressure in the eye which comprises topically administering triamterene to the surface of the eye in an amount effective to reduce the intra-ocular pressure therein. The triamterene will be present in a complication as hereindescribed.

Further, the present invention provides a unit dose of a liquid topical composition of the invention having a volume from 0.01 to 0.8 ml (i.e. a drop of 10 to 80 microliters) and containing from 1 microgramme to 1.6 mg of triamterene and more usually 0.02 to 0.05 ml and containing 2 microgrammes to 1 mg. of triamterene.

If desired other anti-glaucoma agents may be included in the composition of this invention. Generally this is not desired since although an increase in maximum pressure fall may occur there is a possibility that the side effect of the other anti-glaucoma agent may appear.

The present invention provides a phramaceutical composition adapted for administration to the eye which composition contains triamterene and an intra-ocular pressure lowering drug selected from the group consisting of sympathomimetic agents, β-adrenergic blocking agents and cholinergic agonists.

In an apt form the present invention provides a pharmaceutical composition adapted for administration to the eye which composition contains triamterene and a sympathomimetic agent.

Suitable sympathomimetic agents for use in such co-formulations include adrenaline or a pharmaceutically acceptable salt thereof. Suitable salts include those with hydrochloric, tartaric or boric acids. Suitably the adrenaline is present as a free base. Preferably the adrenaline is in the form of the acid tartrate salt.

Suitably the composition will contain from 0.01 to 2% of sympathomimetic agent, more suitably will contain from 0.05 to 1.5% and preferably from 0.1 to 1.0%.

In a second apt form the present invention provides a pharmaceutical composition adapted for administration to the eye which composition contains triamterene and a β-adrenergic blocking agent.

Suitable β-adrenergic blocking agents for use in such co-formulations include timolol or a pharmaceutically acceptable salt thereof. Preferably timolol is present as its maleate salt.

Suitably the coformulation will contain from 0.01 to 2% of the β-blocking agent, more suitably will contain from 0.5 to 1.5% and preferably from 0.1 to 1.0%.

In a third apt form the present invention provides a pharmaceutical composition adapted for administration to the eye which composition contains triamterene and a cholinergic agonist.

Suitable cholinergic agonists for use in such co-formulations include pilocarpine or a pharmaceutically acceptable salt thereof. Suitable salts include those with hydrochloric of nitric acids. Preferably the cholinergic agonist is pilocarpine nitrate.

Suitably the coformulation will contain from 0.1 to 10% of cholinergic agonist, more suitably will contain 0.5 to 8% and preferably from 1 to 6% of cholinergic agonist.

Suitably the co-formulation of the present invention will contain from 0.01 to 1% of triamterene, more suitably will be 0.02 to 0.75% and preferably from 0.05 to 0.5%.

The forms taken by the compositions of this invention may be as described hereinbefore.

The compositions of this invention are most aptly provided in a multidose container from which drops may be dispensed into the eye. Such containers are well known in the art for dispensing of liquid drops into the eye and such conventional containers may be employed. Most aptly such containers are adapted to hold 1 to 20 mls, more usually 2 to 12 mls. and preferably 3 to 10 mls.

A favoured aspect of the present invention therefore comprises a container adapted to deliver drops of an aqueous solution or an aqueous suspension of this invention as hereinbefore described. A preferred container comprises a glass bottle having a screw cap. This screw cap being replaced by a screw cap carrying a drop forming portion when in use. A second preferred container comprises a plastic bottle, for example of a low density polyethylene, having an integral dispensing tip covered by a screw cap. Such preferred containers are adapted to hold 1 to 20 mls of the composition and preferably 3 to 10 mls of the composition, for example 5, 7.5 or 10 mls. A third preferred type of container adapted to deliver drops holding from 1 to 2.5 mls of composition is made from polypropylene or other heat stable material whereby the whole package may be filled and sealed prior to sterilisation by autoclaving.

From the foregoing it will be appreciated that this invention provides a pharmaceutical composition adapted for topical administration to the human eye in the treatment of glaucoma, the composition comprising triamterene as an active ingredient and a topically administratable carrier including optionally one or more other adjuvants, the proportions and nature of the carrier and other adjuvant or adjuvants and the proportion of triamterene being so mutually selected as to provide a composition which contains a therapeutically effective amount of triamterene yet is sterile, non-irritant and non-toxic to the human eye.

As previously indicated the certain favoured forms of the composition of this invention are aqueous solutions which also contain sufficient of a tonicity adjusting agent (as adjuvant) certain other favoured forms of the composition are aqueous solutions which contain a preservative (as adjuvant). Preferred compositions of this invention are aqueous solutions which are preserved and are substantially isotonic.

The compositions of the present invention may be prepared by conventional means of mixing and blending. Sterile solutions of compositions of the present invention may be prepared by filtration of the solution through a cellulose ester membrane having a pore size of 0.22 microns or by heat sterilisation for example, by autoclaving. Sterile suspensions of compositions of the present invention may be prepared by mixing together the pre-sterilised components under aseptic conditions. The containers for delivering drops of sterile compositions of the invention are conventionally pre-sterilised and filled under aseptic conditions with the sterile composition using conventional metering pumps capable of delivering from 1 to 20 mls. each filling cycle.

The compositions of this invention are non-irritant, that is they do not cause unacceptable irritation to the eye when applied topically. Most aptly the compositions are bland upon application.

In the following Examples percentages referred to are expressed in terms of weight/volume.

EXAMPLE 1

Triamterene Suspension Formulation

The suspension was formulated as follows:

| | |
|---|---|
| Triamterene | 0.5% |
| *Polyoxypropylene-polyoxyethylene diol block copolymer MW 4375 | 0.05% |
| +Polyacrylic acid cross-linked with triallyl sucrose | 0.075% |
| Sodium chloride | 0.75% |
| Benzalkonium chloride | 0.002% |
| Sodium hydroxide solution to adjust the pH to 7 | |
| Distilled water to | 100% |

*Pluronic L64
+Carbopol 941

The preparation of a sterile suspension was carried out as follows. Triamterene powder was heated at 160° C. for 1 hour, sufficient for dry heat sterilisation, allowed to cool and stored under aseptic conditions.

The Pluronic L64 was dissolved in 25 ml of water using stirring. The Carbopol 941 was then dispersed in the rest of the water using stirring. When the Carbopol was fully dispersed it was filtered under pressure through a millipore 10 micron filter. The Pluronic solution was then added to the filtered Carbopol dispersion. The Carbopol was then neutralised with sodium hydroxide solution and the sodium chloride and benzalkonium chloride dissolved in this neutralised solution and the final volume adjusted to 100 ml. The final formulation was made sterile by autoclaving at 116° C. for 30 minutes and then allowed to cool.

The remaining procedures were carried out in aseptic conditions under a laminar flow hood.

The sterile triamterene powder was triturated in a pestle and mortar with a portion of Carbopol solution. This suspension was quantitatively added to the remaining Carbopol solution and mixed thoroughly.

The suspension was then aseptically filled into sterile amber glass bottles to provide a sterile suspension using an eye dropper.

Similar formulations may be prepared replacing the sodium chloride with an equiosmotic amount of glycerol and/or replacing the benzalkonium chloride with phenylethanol.

EXAMPLE 2

Triamterene Suspension Formulation

The suspension was formulated as follows:

| | |
|---|---|
| Triamterene | 0.5% |
| Polyoxypropylene-polyoxyethylene diol block copolymer (molecular weight 4375)* | 0.05% |
| Polyacrylic acid cross-linked with triallyl sucrose** | 0.075% |
| Phenylethanol | 0.50% |
| Thiomersal | 0.01% |
| Sodium hydroxide solution to adjust the pH to 7 | |
| Distilled water to | 100% |

*The diol block copolymer was Pluronic L64
**The polyacrylic acid was Carbopol 941

The preparation of the suspension was carried out as described in Example 1.

EXAMPLE 3

Triamterene Solution Formulation

The solution was formulated as follows:

| | |
|---|---|
| Triamterene | 0.1% |
| Polyvinylpyrrolidone* (M.W. 2500) | 50% |
| Phenylmercuric nitrate | 0.002% |
| Sodium hydroxide solution to adjust the pH to 7 | |
| Distilled water to | 100% |

*The polyvinyl pyrrolidone used was Kollidon 12PF

The polyvinyl pyrrolidone was dissolved in water (to give 90 ml). The triamterene was then added to the solution of polyvinyl pyrrolidone and stirred until dissolved. The preservative was then added and the pH of the solution adjusted to pH 7 with an aqueous solution of sodium hydroxide. The volume of the solution was then made up to 100 ml with distilled water.

The final solution may be sterilised by filtration through a 0.22 micron cellulose ester membrane filter (Millipore, Bedford Mass) or by autoclaving at 116° C. for 30 minutes. The sterile solution may be aseptically filled into sterile eye dropper bottles.

EXAMPLE 4

Triamterene Solution Formulation

| | |
|---|---|
| Triamterene | 0.01% |
| Polyvinyl pyrrolidone (MW 2500)* | 20% |
| Disodium hydrogen phosphate | 0.03% |
| Potassium dihydrogen phosphate | 0.018% |
| Sodium hydroxide solution to adjust pH to 7 | |
| Distilled water to | 100% |

*Kollidon 12PF

The polyvinyl pyrrolidone was dissolved in water (to give 90 ml) with stirring. The phosphate buffer system was then dissolved in this solution and finally the triamterene was dissolved with stirring. The pH of the solution was adjusted to pH 7 with sodium hydroxide solution and the volume of the solution made up to 100 ml with distilled water.

The solution may be sterilised by filtration through a 0.22 micron cellulose ester membrane filter or by autoclaving at 116° C. for 30 minutes.

The sterile solution may then be filled under aseptic conditions into sterile eye dropper bottles.

EXAMPLE 5

Triamterene Solution Formulation

| | |
|---|---|
| Triamterene | 0.01% |
| Polyethylene glycol (M.W. 6000)* | 20.00% |
| Disodium hydrogen phosphate | 0.04% |
| Potassium dihydrogen phosphate | 0.024% |
| Sodium hydroxide solution to adjust pH to 7 (if necessary) | |
| Distilled water to | 100% |

*Carbowax 6000

After dissolving the polyethylene glycol in water (to give 90 ml) the procedure was followed as described in Example 4.

EXAMPLE 6

Triamterene Solution Formulation

The solution was formulated as follows:

| | |
|---|---|
| Triamterene | 0.01% |
| Polyvinyl pyrrolidone (number average molecular weight 40,000) | 15.0% |
| Propylene glycol | 1.23% |
| Potassium dihydrogen phosphate | 0.05% |
| Disodium hydrogen phosphate | 0.03% |
| Phenyl ethanol | 0.5% |
| Distilled water to adjust volume to | 100% |

The polyvinyl pyrrolidone was dissolved in distilled water (70 ml) with stirring. On dissolution propylene glycol, the buffer system of potassium dihydrogen phosphate and disodium hydrogen phosphate and the preservative phenyl ethanol were then added to the solution. Finally the triamterene was added and stirred until dissolved. The pH value of the solution was adjusted to give a pH value of 7. The volume of the solution was adjusted to 100 ml. by the addition of distilled water. The final solution was a clear liquid buffered at pH 7.

This solution may be sterilised by filtration through a 0.22 micron cellulose ester membrane filter or by autoclaving at 116° C. for 30 minutes. The sterilised solution may be filled into sterile eye dropper bottles under aseptic conditions.

EXAMPLE 7

Triamterene Solution Formulation

The solution was formulated as follows:

| | |
|---|---|
| Triamterene | 0.01% |
| Polyvinyl pyrrolidone (number average molecular weight 2,500) | 20.0% |
| Propylene glycol | 1.1% |
| Potassium dihydrogen phosphate | 0.05% |
| Disodium hydrogen phosphate | 0.03% |
| Phenyl ethanol | 0.5% |
| Distilled water to adjust volume to | 100% |

The solution was prepared in a similar manner to that used for Example 6. The clear solution buffered to pH 7 may also be sterilised and packaged in a similar manner.

EXAMPLE 8

Triamterene Solution Formulation

The solution was formulated as follows:

| | |
|---|---|
| Triamterene | 0.01% |
| Polyvinyl pyrrolidone (number average molecular weight 2,500) | 10.0% |
| Polyethylene glycol (molecular weight 6000) | 10.0% |
| Propylene glycol | 0.85% |
| Potasssium dihydrogen phosphate | 0.05% |
| Disodium hydrogen phosphate | 0.03% |
| Phenyl ethanol | 0.5% |
| Distilled water to adjust the volume to | 100% |

The solution was prepared in a similar manner to that used for Example 6. The clear solution buffered to pH 7 may also be sterilised and packaged in a similar manner.

EXAMPLE 9

Triamterene Solution Formulation

The solution was formulated as follows:

| | |
|---|---|
| Triamterene | 0.01% |
| Polyethylene glycol (molecular weight 6000) | 20.0% |
| Propylene glycol | 0.6% |
| Potassium dihydrogen phosphate | 0.05% |
| Disodium hydrogen phosphate | 0.03% |
| Phenyl ethanol | 0.5% |
| Distilled water to adjust the volume to | 100 ml. |

The solution was prepared in a similar manner to that described in Example 6. The clear solution buffered to pH 7 may also be sterilised and packaged in a similar manner.

EXAMPLE 10

Triamterene Solution Formulation

The solution was formulated as follows:

| | |
|---|---|
| Triamterene | 0.045% |
| *Polyoxypropylene-polyoxyethylene diol block copolymer molecular | 30.0% |

-continued

| | weight 4375 | |
|---|---|---|
| | Propylene glycol | 0.8% |
| | Potassium dihydrogen phosphate | 0.03% |
| | Disodium hydrogen phosphate | 0.05% |
| | Phenyl ethanol | 0.5% |
| | Distilled water to adjust the volume to | 100% |

*The block copolymer used was Pluronic L64.

The solution was prepared in a similar manner to that described in Example 6. The clear solution buffered to pH 7 may also be sterilised and packaged in a similar manner.

EXAMPLE 11

Triamterene Suspension Formulation

The suspension was formulated as follows:

| Triamterene | 0.5% |
|---|---|
| Sodium dihydrogen phosphate | 0.16% |
| Disodium hydrogen phosphate | 0.76% |
| Glycerol | 1.8% |
| Benzalkonium chloride | 0.01% |
| Distilled water to adjust the volume to | 100% |

The sterile, preserved, buffered suspension was prepared as follows. Triamterene powder was heated at 160° C. for 1 hour, sufficient for dry heat sterilisation, allowed to cool and stored under aseptic conditions. The sodium dihydrogen phosphate, glycerol and benzalkonium chloride were dissolved in distilled water (90 ml). The volume of the solution was then adjusted to 100 ml by addition of distilled water. This solution may then be sterilised either by filtration through a 0.22 micron cellulose ester membrane filter or by autoclaving for 30 minutes. The solution was sterilised by autoclaving at 116° C. for 30 minutes and the solution allowed to cool.

The remaining procedures were carried out in aseptic conditions under a laminar flow hood.

The sterile triamterene powder was triturated in a pestle and mortar with a portion of the sterile solution. The resultant suspension was added quantitatively to the remaining sterile solution and mixed thoroughly.

The suspension was then aseptically filled into sterile amber glass bottles to provide a sterile suspension of triamterene suitable for multidose application using an eye dropper.

EXAMPLES 12–18

Triamterene Solution Formulations

A series of triamterene solutions in which the triamterene is solubilised by organic acids alone and together with polymeric solubilising agents were prepared and assessed for their ability to lower intra-ocular pressure in the rabbit by topical application. The solutions were prepared by dissolving the solubilising agents in water, adding triamterene and warming and stirring the mixture until the triamterene had dissolved. The examples are as follows:

| Example | Triamterene % | glutamic acid % | lactic acid % | polymer |
|---|---|---|---|---|
| 12 | 0.1 | 0.1 | — | — |
| 13 | 0.1 | 0.1 | — | polyethylene glycol M.W. 400, 10% |
| 14 | 0.2 | 0.25 | — | — |
| 15 | 0.2 | 0.25 | — | Polyoxypropylene-polyoxyethylene diol block copolymer M.W. 4375, 10% |
| 16 | 0.1 | — | 0.1 | — |
| 17 | 0.2 | — | 0.2 | — |
| 18 | 0.1 | — | 0.08 | polyvinyl pyrrolidone M.W. 2,500, 15% |

EXAMPLES 19–26

Triamterene Solution Formulations

A series of triamterene solutions in which the triamterence is solubilised by xanthine derivatives were prepared and assessed for their ability to lower intra-ocular pressure in the rabbit by topical application. The solutions were prepared by dissolving the solubilising agents in water, adding triamterene and warming and stirring the mixture to facilitate the dissolution of the triamterene. The examples are as follows:

| Example | Triamterene % | Dyphylline % | Proxyphylline % | Other ingredients |
|---|---|---|---|---|
| 19 | 0.4 | 5 | — | — |
| 20 | 0.3 | — | 10 | — |
| 21 | 0.15 | — | 5 | — |
| 22 | 0.15 | — | 5 | Benzalkonium chloride 0.01% |
| 23 | 0.15 | — | 5 | Lactic acid to pH 6 |
| 24 | 0.1 | 5 | — | Phosphate buffer to pH 7 |
| 25 | 0.15 | — | 6 | Phosphate buffer to pH 7 |
| 26 | 0.15 | — | 6 | Benzalkonium chloride 0.04% Phosphate buffer to pH 7 |

EXAMPLE 27

Triamterene Solution Formulation

The solution was formulated as follows:

| Triamterene | 0.15% |
|---|---|
| Proxyphylline | 6.0% |
| Potassium dihydrogen phosphate | 0.36% |
| Disodium hydrogen phosphate $2H_2O$ | 0.70% |
| Phenyl ethanol | 0.5% |
| Distilled water to adjust the volume to | 100% |

The proxyphylline, potassium dihydrogen phosphate, disodium hydrogen phosphate, phenyl ethanol were dissolved in distilled water (80 ml) with stirring. The triamterene was added to this solution and the mixture stirred and warmed to 50° C. to ease the dissolution of the triamterene. On cooling the volume of the solution was adjusted to 100 ml by addition of distilled water. The final solution was clear and buffered at pH 7.

This solution may be sterilised by filtration through a 0.22 micron cellulose ester membrane filter or by autoclaving at 116° C. for 30 minutes. The sterilised solution

EXAMPLE 28

Triamterene Solution Formulation

The solution was formulated as follows:

| | |
|---|---|
| Triamterene | 0.15% |
| Proxyphylline | 5.0% |
| Benzalkonium chloride | 0.01% |
| Lactic acid solution, 10% to adjust the pH to 6 | |
| Distilled water to adjust volume to | 100 ml. |

The proxyphylline and benzalkonium chloride were dissolved in distilled water (80 ml). The triamterene was added to this solution and the mixture stirred and warmed gently until the triamterene dissolved. The solution was allowed to cool and the pH value of the solution adjusted to 6 by addition of 10% lactic acid solution. The final volume of this solution was adjusted to 100 ml. by the addition of distilled water. The resultant solution was a clear liquid which was substantially isotonic water tear fluid.

This solution may be sterilised by filtration through a 0.22 micron cellulose ester membrane filter or by autoclaving at 116° C. for 30 minutes. The sterile solution may then be filled into sterile eye-dropper bottles under aseptic conditions.

EXAMPLE 29

Triamterene Solution Formulation

The solution was formulated as follows:

| | |
|---|---|
| Triamterene | 0.1% |
| Dyphylline | 5.5% |
| Potassium dihydrogen phosphate | 0.36% |
| Disodium hydrogen phosphate 2H$_2$O | 0.70% |
| Benzalkonium chloride | 0.01% |
| Distilled water to adjust volume to | 100 ml. |

The dyphylline, potassium dihydrogen phosphate, disodium hydrogen phosphate, benzalkonium chloride were dissolved in water (80 ml). The triamterene was added to this solution and the mixture warmed to 50° C. with stirring to facilitate the dissolution of the triamterene. On cooling the volume of the solution was adjsuted to 100 ml. by addition of distilled water. The final solution was a clear liquid, buffered at pH 7 and had a tonicity which was substantially the same as that of tear fluid.

EXAMPLE 30

Preparation of a Multidose Pack of Triamterene Solution

A solution of triamterene was prepared in a similar manner to that described in Example 28. The following operations were then carried out under aseptic conditions. The solution was filtered through a 0.22 micron cellulose ester membrane filter (available from Millipore Corp., Bedford, Mass.). The now sterile solution was filled into open-necked sterile low density polyethylene bottles using a conventional automatic metering pump capable of delivering a charge of 10 ml. of solution per filling cycle. The drop forming portion of the multi-dose pack was then fixed into the neck of the polyethylene bottle. The dropper bottle was then capped and sealed with a conventional plastic screw cap with a tamper-proof sealing strip. The components of the multi-dose pack were sterilised by gamma-irradiation at 2.5 Mrads and stored under aseptic conditions until required. This solution in the multidose pack would be sterile until opened for use. This solution may be applied as drops topically to the eye for the purpose of reducing the intra-ocular tension therein 3 or 4 times each day or as directed by a physician for a period of time, for example up to 30 days.

EXAMPLE 31

Preparation of a Multi-dose Pack of Triamterene Solution

A solution of triamterene was prepared in a similar manner to that described in Example 28. The solution was filtered through a 0.45 micron cellulose ester membrane filter (available from Millipore Corp., Bedford, Mass.). The solution was then filled into amber glass bottles by means of a conventional automatic metering pump capable of delivering a charge of 7.5 ml. of solution per filling cycle. The bottle was then capped in a conventional manner with a screw cap. The bottle and its contents were then sterilized by autoclaving at 116° C. for 30 minutes. In use the screw cap of the bottle may be removed and substituted by an eye dropper which had been previously packed and sterilised.

EXAMPLE 32

Triamterene-Adrenaline Formulation

A composition containing triamterene in the form of a solution together with adrenaline may be formulated as follows:

| | |
|---|---|
| Triamterene | 0.1 g |
| Adrenaline | 0.5 g |
| Polyvinyl pyrrolidone (number average mol. wt. 2,500) | 50 g |
| Distilled water to | 100 ml. |

The polyvinyl pyrrolidone may be dissolved in water (40 ml). The adrenaline may be added to this solution and stirred until dissolved. The triamterene may be dissolved in this solution with stirring and the volume of the resulting solution adjusted to 100 ml by addition of distilled water.

Similar formulations may be prepared using adrenaline acid tartrate in place of adrenaline.

EXAMPLE 33

Triamterene-Timolol Maleate Formulation

A composition containing triamterene in the form of a solution together with timolol maleate may be formulated as follows:

| | |
|---|---|
| Triamterene | 0.1 g |
| Timolol maleate | 0.25 g |
| Polyvinyl pyrrolidone (number average molecular weight 2,500) | 50 g |
| Distilled water to | 100 ml. |

The polyvinyl pyrrolidone may be dissolved in water (40 ml). The timolol maleate may be added to this solution and stirred until dissolved. The triamterene may be dissolved in this solution with stirring and the volume of the resulting solution adjusted to 100 ml by addition of distilled water.

EXAMPLE 34

Solubilisation of Triamterene

The solubilising ability of xanthine derivatives exemplified by caffeine, dyphylline and proxyphylline were measured (a) with variation of xanthine concentration, (b) with variation of pH value and (c) with various concentrations of xanthine derivative together with various concentrations of polyvinyl pyrrolidone, molecular weight 2,500. The solubilising ability was expressed in relation to the concentration of triamterene in a saturated solution at 5° C. The concentrations were measured as follows, an aqueous solution of the solubilising agent of appropriate strength was prepared. A portion of this solution was taken and a slight excess of triamterene powder was added. The mixture was stirred vigorously whilst warming on a magnetic stirrer hot plate until no more solid dissolved. The mixture was then allowed to cool and stand overnight at 5° C. The pH of the solution was then measured. The solid was then filtered off by passage through a 0.45 micron cellulose ester membrane filter, the first 10 mls. being discarded and the next 25 ml. of solution collected for analysis. The concentration of triamterene in this solution was measured by U.V. absorbtion spectrometry and 370 nm by comparison with a previously derived calibration curve of triamterene in 2.5% polyethylene glycol solution.

In determining the solubility in relation to variation of pH the initial solution was adjusted to pH 4.5 by addition of 0.2% lactic acid and subsequent pH values obtained by neutralisation with N sodium hydroxide solution.

The results are shown in the accompanying tables 1, 2 and 3.

TABLE 1

Solubility of Triamterene in Aqueous Solutions of Xanthine Derivatives at 5° C.

| Concs. of Xanthine Derivatives % | Proxyphylline Conc. of Triamterene % | pH | Dyphylline Conc. of Triamterene % | pH | Caffeine Conc. of Triamterene % | pH |
|---|---|---|---|---|---|---|
| 1 | 0.013 | 7.3 | 0.012 | 6.85 | 0.022 | 6.4 |
| 2 | 0.027 | 7.2 | 0.029 | 6.75 | | |
| 3 | | | 0.05 | 7.1 | | |
| 4 | | | 0.07 | 7.15 | | |
| 5 | 0.13 | 7.3 | 0.092 | 7.20 | | |
| 10 | 0.300 | 7.4 | 0.22 | 7.35 | | |
| 5% Etophylline | 0.1% Triamterene | | | | | |
| 4% Pentoxyphylline | 0.05% Triamterene | | | | | |

TABLE 2

Solubility of Triamterene in Aqueous Solutions of Lactic Acid and Xanthine Derivatives: Variation with pH value, at 5° C.

| pH Value | 1% Caffeine | 1% Proxy-phylline | 5% Proxy-phylline | 1% Dyphylline | 5% Dyphylline |
|---|---|---|---|---|---|
| 4.50 | 0.30 | | | | |
| 4.65 | | 0.35 | | | |
| 4.70 | | | | 0.25 | 0.41 |
| 4.85 | | 0.21 | | | |
| 5.00 | | | | 0.20 | |
| 5.10 | | 0.15 | | | |
| 5.20 | | | 0.35 | | |
| 5.25 | 0.19 | | | | |
| 5.30 | | | | 0.19 | |
| 5.40 | 0.14 | | | | |
| 5.60 | | | 0.07 | 0.25 | 0.17 | 0.23 |
| 5.70 | 0.08 | | | | |
| 5.80 | | | | | 0.20 |
| 5.90 | | | | | 0.16 |
| 5.95 | | | | 0.15 | |
| 6.05 | | | 0.13 | | |
| 6.10 | | 0.02 | | | |
| 6.25 | | | | 0.12 | |
| 6.40 | | | 0.14 | | |
| 6.50 | | | | 0.10 | |
| 6.60 | | | | | 0.11 |
| 6.70 | | | | 0.07 | |
| 7.20 | 0.02 | | | 0.02 | |
| 8.80 | | 0.01 | | | |

TABLE 3

Solubility of Triamterene in Aqueous Solutions of Polyvinyl Pyrrolidone and Xanthine Derivatives at 5° C.

| Concentration of Polyvinyl pyrrolidone (M.W. 2,500) % | 1.5% Caffeine | 5% Dyphylline | 10% Dyphylline | 5% Proxyphylline |
|---|---|---|---|---|
| 10 | | 0.13 | | |
| 15 | 0.066 | 0.19 | 0.36 | 0.13 |
| 20 | 0.083 | 0.21 | | 0.15 |
| 25 | 0.092 | 0.23 | | 0.22 |
| 30 | 0.13 | 0.25 | | 0.21 |
| 35 | | 0.31 | | 0.22 |
| 50 | | | 0.60 | 0.29 |

EXAMPLE 35

Triamterene Solution Formulation

| | |
|---|---|
| Triamterene | 0.1% |
| Hydroxyethyl theophylline | 5.0% |
| Potassium dihydrogen phosphate | 0.36% |
| Disodium hydrogen phosphate 2H$_2$O | 0.70% |
| Benzalkonium chloride | 0.01% |
| Distilled water | to 100 ml. |

The solution was prepared in a similar manner to that described in Example 29. The final solution was a clear liquid, buffered at pH 7 and had a tonicity which was substantially the same as that of tear fluid.

EXAMPLE 36

Triamterene Solution Formulation

| | |
|---|---|
| Triamterene | 0.145% |
| Hydroxyethyl theophylline | 5.0% |

| -continued | |
|---|---|
| Potassium dihydrogen phosphate | 0.8% |
| Disodium hydrogen phosphate 2H₂O | 0.15% |
| Benzalkonium chloride | 0.01% |
| Distilled water | to 100 ml. |

The solution was prepared in a similar manner to that described in Example 29. The final solution was a clear liquid, buffered at pH 6 and had a tonicity which was substantially the same as that of tear fluid.

EXAMPLE 37

Triamterene Solution Formulation

| Triamterene | 0.3% |
|---|---|
| Hydroxyethyl theophylline | 5.0% |
| Lactic acid 10% solution to pH 5 | |
| Benzalkonium chloride | 0.01% |
| Distilled water | to 100 ml. |

The solution was prepared in a similar manner to that described in Example 28. The final solution was a clear liquid having a pH of 5 and had a tonicity which was substantially the same as that of tear fluid.

EXAMPLE 38

Triamterene Solution Formulation

| Triamterene | 0.19% |
|---|---|
| Dyphylline | 5.5% |
| *Polyoxyethylene-polyoxypropylene diol block copolymer (molecular weight 12,500) | 18.0% |
| Benzalkonium chloride | 0.01% |
| Sodium hydroxide solution or hydrochloric acid solution to adjust the pH to 7 as required. | |
| Distilled water | to 100 ml. |

*The polymer used was Pluronic F127.

The dyphylline, Pluronic F127 and benzalkonium chloride were dissolved in distilled water (70 ml) with stirring. The triamterene was added to this solution and the mixture stirred and warmed to about 50° C. to ease the dissolution of the triamterene. On cooling the pH of the solution was adjusted to pH 7 by addition of sodium hydroxide solution or dilute hydrochloric acid as appropriate. The volume of the solution was adjusted to 100 ml by addition of distilled water. This clear, substantially isotonic solution may be sterilised by filtration through a 0.22 micron filter and aseptically filled into sterile containers ready for use.

EXAMPLE 39

Triamterene Solution Formulation

| Triamterene | 0.145% |
|---|---|
| Dyphylline | 5.5% |
| Polyoxyethylene-polyoxypropylene diol block copolymer (molecular weight 12,500) | 10.0% |
| Benzalkonium chloride | 0.01% |
| Sodium hydroxide or dilute hydrochloric acid to adjust pH to 7 as required. | |
| Distilled water | to 100 ml. |

The solution was prepared in a similar manner to that described in Example 38

EXAMPLE 40

Triamterene Solution Formulation

| Triamterene | 0.15% |
|---|---|
| Dyphylline | 5.5% |
| Polyethylene glycol (Molecular Weight 4,000) | 10.0% |
| Benzalkonium chloride | 0.01% |
| Sodium hydroxide solution or dilute hydrochloric acid to adjust pH to 7.5 as required. | |
| Distilled water | to 100 ml. |

The solution was prepared in a similar manner to that described in Example 38.

Demonstration of Effectiveness 1

A suspension of triamterene in water containing 0.5% by weight of triamterene and 0.80% by weight of hydroxyethyl cellulose suspending agent was employed as test material.

The effect of this suspension on the ocular tension in the eyes of rabbits (New Zealand White/Male) was tested as follows. 50 Microliters of the suspension was applied topically to one eye of the rabbit. The ocular tension of this eye was measured at 1, 2, 4 and 5 hours after application of the suspension. The following Table 1 shows the average results for 8 rabbits together with the ocular tension measured half an hour before application of the suspension.

TABLE 1

| Time (hours) | Ocular Tension (mmHg) |
|---|---|
| −0.5 | 18.2 |
| +1 | 14.5 |
| +2 | 14.5 |
| +4 | 16.0 |
| +5 | 16.7 |

Similar tests were carried out as described above except that the test animals were monkeys (Aoutus trivirgatus/male) and a total of 7 animals were treated and 10 microliters of the suspension were applied to the eye and a further 10 microliters 30 seconds later.

The following Table 2 shows the results obtained, expressed as the reduction in ocular tension (untreated eye minus treated eye at times −0.5, 1, 2, 4 and 5 hours after administration of the suspensions.

TABLE 2

| Time (hours) | Reduction in ocular tension (mm/Hg) |
|---|---|
| −0.5 | 0 |
| +1 | 3.7 |
| +2 | 2.6 |
| +4 | 1.2 |
| +5 | 0.6 |

Demonstration of Effectiveness 2

A solution of triamterene in water containing 0.1% triamterene, 50% polyvinyl pyrrolidone as Kollidon 12PF the pH of the solution being adjusted to pH 7 by sodium hydroxide and the volume made up to 100% using distilled water was used as test material.

The effect of this solution on the ocular tension in the eyes of rabbits (New Zealand White/Male) was tested as follows. 50 microliters of the solution was applied topically to one eye of each rabbit. The ocular tension of both treated and untreated eyes was measured at 1, 2, 4, 5 and 6 hours after the application of the solution. The following Table 3 shows the average results for 6 rabbits together with the ocular tension measured half an hour before application of the solution.

TABLE 3

| Time (hours) | Ocular Tension (mmHg) | |
| --- | --- | --- |
| | Untreated eye | Treated eye |
| −0.5 | 21.6 | 21.8 |
| +1 | 16.6 | 15.2 |
| +2 | 15.6 | 14.3 |
| +3 | 16.9 | 15.9 |
| +5 | 18.8 | 17.7 |
| +6 | 20.3 | 19.1 |

The solution gave a bilateral response and the ocular tension was returning to normal after 6 hours. The solution was not irritant.

Demonstration of Effectiveness 3

A solution of triamterene in water containing 0.01% w/v triamterene, 20% w/v polyvinyl pyrrolidone molecular weight 2500 (Kollidon 12PF) the solution being bufferd at pH 7 using a phosphate buffer was used as test material.

The effect of this solution on the ocular tension in the eyes of rabbits (New Zealand White/Male) was tested as follows. 50 microliters of the solution was applied topically to one eye of each rabbit. The ocular tension of both treated and untreated eyes was measured at 1, 2, 4 and 5 hours after application of the solution. The following table 4 shows the average results for six rabbits together with the ocular tension measured quarter of an hour before application of the solution.

TABLE 4

| Time (hours) | Ocular Tension (mmHg) | |
| --- | --- | --- |
| | Untreated eye | Treated eye |
| −0.25 | 21.3 | 21.0 |
| +1 | 18.6 | 17.4 |
| +2 | 17.6 | 16.8 |
| +4 | 19.4 | 18.9 |
| +5 | 20.2 | 19.7 |

Demonstration of Effectiveness 4

A solution of triamterene in water containing 0.01 w/v triamterene 20% w/v polyethylene glycol molecular weight 6000 (Carbowax 6000), the solution being buffered at pH 7 using a phosphate buffer was used as a test material.

The test method on six different rabbits was that described above in Demonstration of Effectiveness 3. The results achieved are described in Table 5.

TABLE 5

| Time (hours) | Ocular Tension (mmHg) | |
| --- | --- | --- |
| | Untreated eye | Treated eye |
| −0.25 | 21.4 | 21.4 |
| +1 | 17.7 | 16.7 |
| +2 | 17.5 | 16.6 |
| +4 | 19.2 | 18.1 |
| +5 | 20.1 | 19.1 |

Demonstration of Effectiveness 5

The effect of aqueous solutions and aqueous suspensions of triamterene described in the examples on the ocular tension in the eyes of rabbits (New Zealand White/male) was tested as follows. 50 microliters of the triamterene composition was applied topically to one eye of the rabbit. The ocular tension of this eye was measured at 1, 2, 4 and 5 hours after the application of the composition. From the results obtained a value for the maximum mean fall in intra-ocular pressure from the group of rabbits used in each test was obtained.

| Example No. | Maximum mean fall in intra-ocular pressure (mmHg) |
| --- | --- |
| 3 | 5.5 |
| 10 | 4.2 |
| 11 | 5.0 |
| 12 | 4.9 |
| 13 | 4.8 |
| 14 | 5.1 |
| 15 | 5.4 |
| 16 | 4.6 |
| 17 | 5.9 |
| 18 | 4.4 |
| 19 | 6.9 |
| 20 | 6.7 |
| 21 | 5.3 |
| 22 | 6.5 |
| 23 | 5.5 |
| 24 | 5.0 |
| 25 | 5.0 |
| 26 | 7.1 |
| 28 | 7.2 |
| 29 | 6.9 |

Demonstration of Effectiveness 6

The effect of the combination on the ocular tension in the eyes of rabbits (New Zealand White/Male) was tested as follows. Single doses of 50 microliters of 0.1% triamterene suspension, 0.5% adrenaline solution, 0.25% timolol maleate solution were applied either alone or triamterene in combination with one of the other two to one eye of each rabbit in each experiment. The ocular tension in the treated eye was measured before treatment and hourly for up to 5 hours after treatment. The results expressed as mean maximum tension falls are shown in the table. The table shows the increased effect when a combined treatment was given.

| Expt. No. | Treatment Group 1 | Mean Maximum Pressure Fall | Treatment Group 2 | Mean Maximum Pressure Fall |
| --- | --- | --- | --- | --- |
| 1 | 0.5% Adrenaline solution | 5.2 mmHg | 0.5% Adrenaline soln. | 4.9 mmHg |
| 2 | 0.1% Triamterene suspension | 4.3 mmHg | 0.1% Triamterene suspn. | 4.6 mmHg |
| 3 | 0.1% Triamterene suspension | 4.8 mmHg | 0.1% Triamterene suspn. 0.5% Adrenaline soln. | 6.0 mmHg |
| 4 | 0.25% Timolol maleate solution | 4.0 mmHg | 0.25% timolol maleate solution | 3.6 mmHg |
| 5 | 0.1% Triamterene suspension | 4.8 mmHg | 0.1% Triamterene suspn. 0.25% timolol maleate | 6.6 mmHg |

| Expt. No. | Treatment Group 1 | Mean Maximum Pressure Fall | Treatment Group 2 | Mean Maximum Pressure Fall |
|---|---|---|---|---|
| | | | solution | |

Demonstration of Effectiveness 7

A study on the ability of a 0.5% aqueous suspension of triamterene to lower the intra-ocular pressure in fifteen human patients suffering from bilateral chronic simple open-angle glaucoma was carried out. A single drop of the suspension was instilled in one eye of each patient. The intra-ocular pressure was measured in the treated and untreated eye immediately before treatment and post-treatment at 30 minutes, 1, 2, 4 and 6 hours. The mean maximum reduction in intra-ocular pressure for the group of patients was 6.4 mmHg and the maximum mean reduction at 6 hours post-treatment was 4.7 mmHg.

What we claim is:

1. A method for reducing the intra-ocular pressure in the eye of a patient having glaucoma which comprises topically applying to the surface of the eye a sterile, aqueous solution comprising an effective intra-ocular pressure reducing amount of triamterene rendered soluble by an effective solubilizing amount of a water soluble xanthine.

2. A method according to claim 1 in which the aqueous solution contains from 0.05 to 0.4% of triamterene.

3. A method according to claim 1 in which the aqueous solution contains from 0.1 to 0.3% of triamterene.

4. A method according to claim 1 in which the aqueous solution contains from 0.1 to 10% of a xanthine.

5. A method according to claim 1 in which the aqueous solution contains from 1 to 8% of a xanthine.

6. A method according to claim 4 in which the xanthine is proxyphylline.

7. A method according to claim 4 in which the xanthine is dyphylline.

8. A method according to claim 4 in which the xanthine is hydroxyethyl theophylline.

9. A method according to claim 1 in which the aqueous solution is rendered substantially isotonic.

10. A method according to claim 1 in which the pH of the aqueous solution is 6.0 to 8.5.

11. A method according to claim 1 in which the aqueous solution contains an effective amount of a preservative.

12. A method according to claim 1 in which the preservative is a quaternary ammonium compound.

13. A method according to claim 12 in which the preservative is benzalkonium chloride.

14. A method according to claim 13 in which the aqueous solution contains from 0.005 to 0.04% of benzalkonium chloride.

15. A method according to claim 1 in which the aqueous solution contains a buffer to give the solution a pH of between 5.0 and 8.0.

16. A method according to claim 1 in which the aqueous solution contains an effective amount of a further solubilizing agent capable of increasing the amount of triamterene in the aqueous solution.

17. A sterile, aqueous solution for reducing the intra-ocular pressure in the eye of a patient having glaucoma adapted for topical application to the eye which comprises an effective intra-ocular pressure reducing amount of triamterene rendered soluble by an effective solubilizing amount of a water soluble xanthine.

18. An aqueous solution according to claim 17 which contains from 0.05 to 0.4% of triamterene.

19. An aqueous solution according to claim 17 which contains from 0.1 to 10% of a water-soluble xanthine.

20. An aqueous solution according to claim 19 in which the xanthine is dyphylline.

21. An aqueous solution according to claim 19 in which the xanthine is proxyphylline.

22. An aqueous solution according to claim 19 in which the xanthine is hydroxyethyl theophylline.

23. An aqueous solution according to claim 17 in which the aqueous solution is rendered substantially isotonic.

24. An aqueous solution according to claim 17 in which the pH of the aqueous solution is 6.0 to 8.5.

25. An aqueous solution according to claim 17 which contains an effective amount of a preservative.

26. An aqueous solution according to claim 25 in which the preservative is a quaternary ammonium compound.

27. An aqueous solution according to claim 26 in which the preservative is benzalkonium chloride.

28. An aqueous solution according to claim 27 which contains from 0.005 to 0.04% benzalkonium chloride.

29. An aqueous solution according to claim 17 which contains a buffer to give the solution a pH of between 5.0 and 8.0.

30. An aqueous solution according to claim 17 which contains an effective amount of a further solubilizing agent capable of increasing the concentration of triamterene in the aqueous solution.

* * * * *